US00PP28671P3

(12) United States Plant Patent
Olesen

(10) Patent No.: US PP28,671 P3
(45) Date of Patent: Nov. 21, 2017

(54) *CLEMATIS* PLANT NAMED 'EVIPO059'

(50) Latin Name: *Clematis viticella*
Varietal Denomination: Evipo059

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 56 days.

(21) Appl. No.: 14/756,263

(22) Filed: Aug. 20, 2015

(65) Prior Publication Data

US 2017/0055421 P1 Feb. 23, 2017

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS http://poulsenroser.com/media/63344/Clematis-2012-2013_Poulsen-Roser_LR_GBP.pdf, "Perfection by Poulsen *Clematis* Main varieties 2013".*
UPOV hit on *Clematis* plant named 'Evipo059', QZ PBR 43290, published Dec. 15, 2014.*

* cited by examiner

*Primary Examiner* — Anne Grunberg

(57) ABSTRACT

A new *Clematis* plant with a compact growth habit, profuse, lavender purple flowers with a distinct purple central bar, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification:
Genus: *Clematis.*
Species: *viticella.*
Variety Denomination: 'Evipo059'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 1999 and the resulting seeds were planted the following winter in a controlled environment in Guernsey, Channel Islands, United Kingdom. The new variety named 'Evipo059' originated as a single seedling from the stated cross.

The new *clematis* plant may be distinguished from its female seed parent and male pollen parent by the following characteristics. The female seed parent has lavender flowers while the newly claimed plant has lavender purple flowers with a purple central bar. The male pollen parent is less compact than the newly claimed plant.

The objective of the hybridization of this *clematis* plant was to create a new and distinct variety for nursery culture with unique qualities such as:

1. Uniform and abundant lavender purple flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo059' was selected by Mogens N. Olesen and Raymond J. Evison in their *clematis* development program in the Channel Islands, United Kingdom in 2000. Asexual reproduction of 'Evipo059' by means of vegetative cuttings and traditional layering was first performed by Mogens N. Olesen and Raymond J. Evison in the nursery during the summer of 2000. This initial and subsequent asexual propagations have demonstrated that the characteristics of 'Evipo059' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo059'. Specifically illustrated in the drawing are flowers at various stages of development, flower in parts, leaves, and stems. Plants shown are 2 years of age.

DETAILED DESCRIPTION OF THE VARIETY

The following is a detailed description of 'Evipo059', as observed in its growth throughout the flowering period in Yamhill County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo026' described and illustrated in U.S. Plant patent application Ser. No. 13/986,920 are compared to 'Evipo059' in Chart 1.

CHART 1

| | 'Evipo059' | 'Evipo026' |
|---|---|---|
| Flower diameter | 100 mm | 90 mm |
| Tepal upper surface | Violet Group N88B with a central bar of Purple Group N79C | Violet Blue Group N92B at margins with mid-tepal coloration of Violet Blue Group 92A |
| Tepal count | 7 to 8 | 8 to 9 |

FLOWER AND FLOWER BUD

Blooming habit: Continuous. The natural flowering period is generally from April to September.

Flower bud:

*Size*.—Normally 27 mm in length. Bud diameter is 14 mm.

*Texture*.—Pubescent.

*Bud form*.—Broad based elliptic.

*Bud color*.—Yellow-Green Group 144C.

Peduncle:

*Surface texture*.—Pubescent.

*Length*.—On average 10 mm.

*Diameter*.—1 mm.

*Color*.—Green Group 143D.

*Strength*.—Moderately strong.

Receptacle:

*Surface texture*.—Lightly pubescent.

*Shape*.—Broad funnel.

*Size*.—1 mm (h)×3 mm (w).

*Color*.—Green Group 143D.

Flower arrangement:

*Location on vine*.—New and old growth.

*Borne*.—Normally in clusters of 5 to 7 flowers.

Flower bloom:

*Size*.—On average, flowers are 100 mm in diameter and 25 mm in depth.

*Profile*.—Open flowers are flat.

*Fragrance*.—None.

*Lasting quality*.—Flowers normally remain up to 10 days on the plant.

Tepals:

*Tepal color*.—The upper surface is Violet Group N88B with a central bar of Purple Group N79C. The lower surface is Violet Group N88C with a central bar Yellow-Green Group 144D.

*Quantity*.—Normally 7 to 8 tepals.

*Size*.—55 mm in length by 31 mm wide.

*Shape*.—Individual tepal shape is elliptic. The tepal apex is acuminate. The base is acute.

*Apex recurvature*.—None, straight.

*Tepal cross section*.—Flat.

*Margins*.—Entire. Medium undulations of margin observed.

*Persistence*.—Tepals drop off cleanly.

Reproductive organs:

*Arrangement*.—Open.

*Pollen*.—None observed.

*Anthers*.—Size: 8mm in length. Color: Black Group 202A. Quantity: On average, 45.

*Filaments*.—Color: White Group N155A with light intonations of Red-Purple Group 70B. Length: 10 mm.

*Pistils*.—Quantity: On average, 20.

*Styles*.—Color: Green-White Group 157A. Length: 12 mm.

PLANT

Plant form: Climbing.

Plant growth: Compact.

Size: Average 30 cm in height, spread 25 cm.

Stems:

*Color*.—Juvenile stems are Yellow-Green Group 144B. Mature stems are Greyed-Purple 183C.

*Internodes*.—On average, 7 cm between nodes.

*Length*.—Normally 10 cm from the base of the plant to the flowering portion of the stem.

*Diameter*.—Normally 3mm.

*Texture*.—Smooth.

Plant foliage:

*Leaf characteristics*.—Deciduous.

*Arrangement*.—Trifoliate, or pentafoliate.

*Leaf size*.—Compound leaves are normally 150 mm (l)×90 mm (w). Leaflets are normally 50 mm (l)×30 mm (w).

*Abundance*.—On average 1 leaf per 10 cm of stem.

*Leaf color*.—Juvenile upper Yellow Group N144A. Juvenile lower Yellow-Green Group 145A. Mature upper Yellow-Green Group 146A. Mature lower Yellow-Green Group 146B.

*Stipules*.—Absent.

*Petioles*.—Size: Normally 50 mm in length by 1 mm diameter. Texture: Smooth. Color: Greyed-Purple Group 187A.

*Petioloule*.—Size: Normally 10 mm in length by 1 mm diameter. Texture: Smooth. Color: Greyed-Purple Group 187A.

*Leaflet shape*.—Generally elliptic with a broad base. The base is acute/rounded. The apex is acute.

*Margin*.—Entire.

*Surface*.—The upper side is smooth. The lower side is smooth.

*Thickness*.—Average.

*Glossiness*.—Not glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

I claim:

1. A new and distinct variety of *clematis* plant named 'Evipo059', substantially as described and illustrated, due to its abundant lavender purple flowers with a distinct purple central bar, with good keepability, attractive long lasting foliage and compact growth, year round flowering under glasshouse conditions, suitability for production from softwood cuttings in pots, durable flowers and foliage which make the variety suitable for distribution in the floral industry.

* * * * *

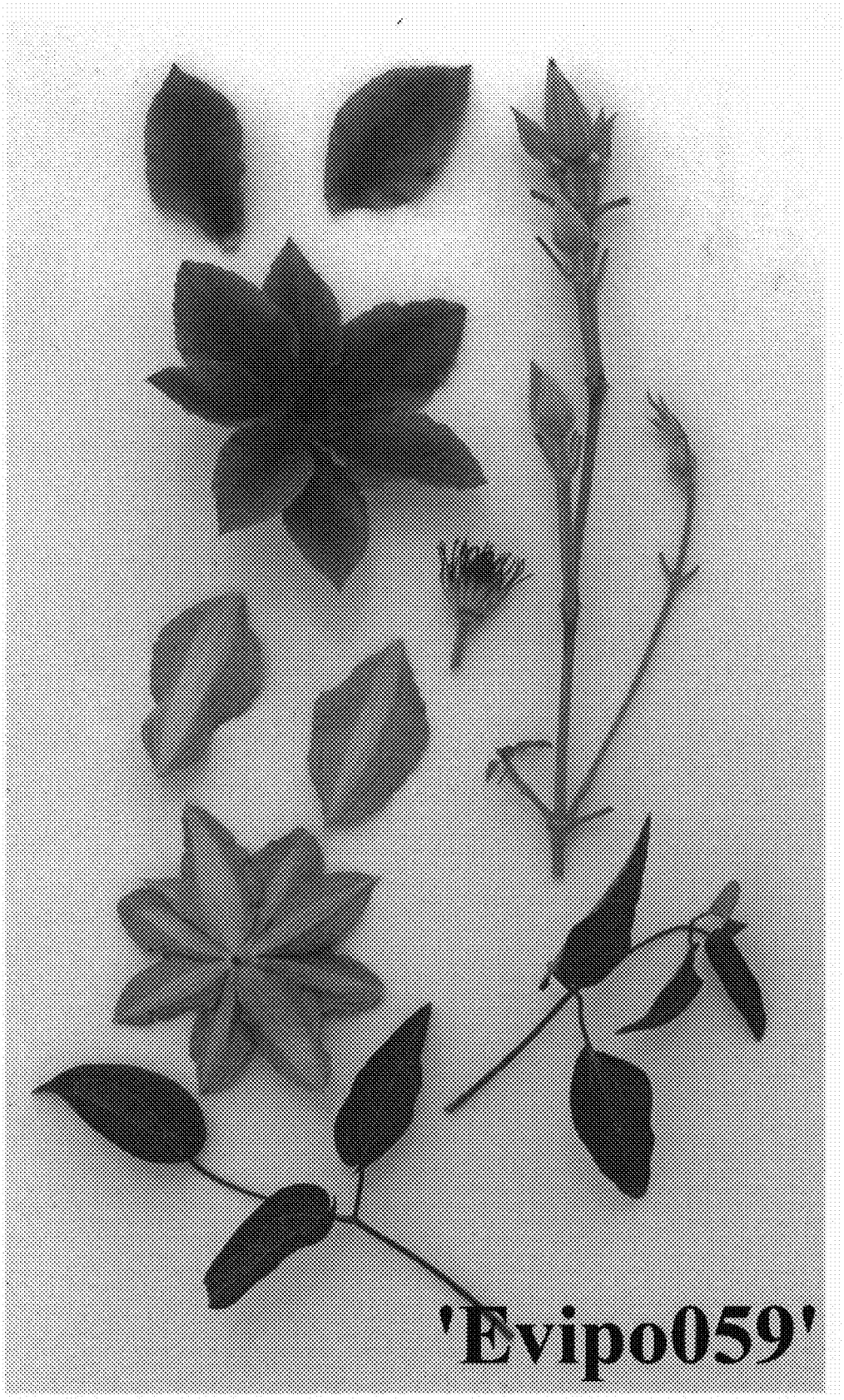
'Evipo059'